(12) United States Patent
Trammell

(10) Patent No.: US 8,093,471 B2
(45) Date of Patent: Jan. 10, 2012

(54) CELERY VARIETY STIX (PYC 6651)

(75) Inventor: Keith W. Trammell, Milwaukie, OR (US)

(73) Assignee: Syngenta Participations AG, Basel (CH)

( * ) Notice: Subject to any disclaimer, the term of this patent is extended or adjusted under 35 U.S.C. 154(b) by 443 days.

(21) Appl. No.: 12/403,310

(22) Filed: Mar. 12, 2009

(65) Prior Publication Data

US 2010/0235953 A1  Sep. 16, 2010

(51) Int. Cl.
*A01H 5/00* (2006.01)
*C12N 5/04* (2006.01)

(52) U.S. Cl. ......... 800/318; 800/295; 800/298; 435/419
(58) Field of Classification Search ....................... None
See application file for complete search history.

(56) References Cited

U.S. PATENT DOCUMENTS

2009/0282506 A1* 11/2009 Pierce ........................... 800/263
* cited by examiner

*Primary Examiner* — Cathy Kingdon Worley
(74) *Attorney, Agent, or Firm* — S. Matthew Edwards

(57) ABSTRACT

A new variety of celery designated as STIX (PYC 6651) and whose seed has an ATCC accession number PTA-9654 is presented. STIX has long petioles that make it well suited for making celery sticks.

8 Claims, 1 Drawing Sheet

CELERY VARIETY STIX (PYC 6651)

FIELD OF INVENTION

The present invention refers generally to the field of plant breeding and in particular to a new variety of celery.

BACKGROUND

The commercial vegetable crop known as celery is widely used in cooking a variety of dishes and is frequently eaten without cooking, for example as a light snack. There are a number of varieties of celery crops. Although these crops of the celery family generally share a similar look and flavor, they differ in specific traits such as petiole size, shape, and number, succulence, ribbiness, disease resistance, shelf life, and bolting pattern, among others.

These specific traits make a celery variety more or less appealing from a commercial standpoint. For example, a variety that is disease resistant and has a longer shelf life is likely to be more commercially valuable than a variety that is susceptible to diseases or has a short shelf life. Also, since the parts of a celery plant that are most commonly consumed are the petioles (or the "stalks"), a variety that produces more or longer petioles is likely to be more desirable than a variety that produces fewer or shorter petioles.

While the pursuit to produce a celery variety that is more appealing for farmers and stores is on-going, it is important that the new varieties retain the flavor, texture, and nutritional properties of the parent plant that is desired by consumers. Thus, search continues for a celery variety that is appealing for consumption while presenting economic advantages to farmers and stores.

SUMMARY

The invention is a variety of celery whose seed has an ATCC number PTA-9654.

DETAILED DESCRIPTION

The crop of the invention is a member of *Apium graveolens* L. of the family Umbelliferae.

Characteristics

PYC 6651 is an exceptionally tall dark green celery with long, medium-smooth, slender petioles. Celeries are often consumed as celery sticks that are approximately four-inches long. PYC 6651 is especially suited for being prepared into approximately-four-inch sticks to be packaged for lunches and snacks. A single petiole of PYC 6651 may give as many as 4 or 5 four-inch cuts, which is significantly more than the 2 or 3 four-inch cuts obtained from a petiole of the shorter, conventional celery varieties. PYC 6651 also carriers a very high level of resistance to the disease *Fusarium oxysporum*.

Stix shows good genetic uniformity, is genetically stable and has remained so for two subsequent generations of seed production.

Some comparison data between PYC 6651 and other varieties are presented in the tables below.

TABLE 1A

LSD Pair-wise Comparison of Seed Stalk Length (Run 1)

| Name of Variety | Mean Seed Stalk Length (cm) | Homogeneous Groups |
|---|---|---|
| PYC 6651 | 15.438 | A |
| Green Bay | 9.012 | B |//

TABLE 1A-continued

LSD Pair-wise Comparison of Seed Stalk Length (Run 1)

| Name of Variety | Mean Seed Stalk Length (cm) | Homogeneous Groups |
|---|---|---|
| Challenger | 6.962 | C |
| Mission | 6.013 | C |

Alpha = 0.05
Standard Error for Comparison = 0.5627
Critical T value = 1.976
Critical Value for Comparison 1.1116
Error term used: Error, 153 DF

TABLE 1B

LSD Pair-wise Comparison of Seed Stalk (Run 2)

| Name of Variety | Mean | Homogeneous Groups |
|---|---|---|
| PYC 6651 | 12.025 | A |
| Green Bay | 9.312 | B |
| Challenger | 8.700 | B |
| Mission | 7.250 | C |

Alpha = 0.05
Standard Error for Comparison = 0.4358
Critical T Value = 1.976
Critical Value for Comparison = 0.8609
Error terms used: Error, 115 DF

TABLE 2A

LSD Pair-wise Comparison of Number of Stalks that are >40 cm (Run 1)

| Name of Variety | Mean | Homogeneous Groups |
|---|---|---|
| PYC 6651 | 11.917 | A |
| Challenger | 10.300 | B |

Alpha = 0.05
Standard Error for Comparison = 0.2419
Critical T Value = 1.981
Critical Value for Comparison = 0.4793
Error term used: Error, 115 DF

TABLE 2B

LSD Pair-wise Comparison of Number of Stalks that are >40 cm (Run 2)

| Name of Variety | Mean | Homogeneous Groups |
|---|---|---|
| PYC 6651 | 11.250 | A |
| Challenger | 9.975 | B |

Alpha = 0.05
Standard Error for Comparison = 0.3148
Critical T Value = 1.992
Critical Value for Comparison = 0.6271
Error term used: Error, 75 DF

TABLE 3A

LSD Pair-wise Comparison of Number of Stalks that are <40 cm (Run 1)

| Name of Variety | Mean | Homogeneous Groups |
|---|---|---|
| PYC 6651 | 3.7667 | A |
| Challenger | 3.8667 | A |

Alpha = 0.05
Standard Error for Comparison = 0.1721
Critical T Value = 1.981
Critical Value for Comparison = 0.3409
Error terms used: Error, 115 DF

TABLE 3B

LSD Pair-wise Comparison of Number of Stalks that are <40 cm (Run 2)

| Name of Variety | Mean   | Homogeneous Groups |
| --------------- | ------ | ------------------ |
| PYC 6651        | 4.0750 | A                  |
| Challenger      | 4.0250 | A                  |

Alpha = 0.05
Standard Error for Comparison = 0.1991
Critical T Value = 1.992
Critical Value for Comparison = 0.3966
Error terms used: Error, 75 DF

TABLE 4A

LSD Pair-wise Comparison of Length (Run 1)

| Name of Variety | Mean   | Homogeneous Groups |
| --------------- | ------ | ------------------ |
| PYC 6651        | 46.100 | A                  |
| Challenger      | 33.200 | B                  |

Alpha = 0.05
Standard Error for Comparison = 0.6212
Critical T Value = 1.981
Critical Value for Comparison = 1.2306
Error terms used: Error, 115 DF

TABLE 4B

LSD Pair-wise Comparison of Length (Run 2)

| Name of Variety | Mean   | Homogeneous Groups |
| --------------- | ------ | ------------------ |
| PYC 6651        | 46.275 | A                  |
| Challenger      | 33.275 | B                  |

Alpha = 0.05
Standard Error for Comparison = 0.7411
Critical T Value = 1.992
Critical Value for Comparison = 1.4763
Error terms used: Error, 75 DF

TABLE 5A

LSD Pair-wise Comparison of Thickness (Run 1)

| Name of Variety | Mean   | Homogeneous Groups |
| --------------- | ------ | ------------------ |
| PYC 6651        | 9.0333 | B                  |
| Challenger      | 9.6833 | A                  |

Alpha = 0.05
Standard Error for Comparison = 0.2777
Critical T Value = 1.981
Critical Value for Comparison = 0.5501
Error terms used: Error, 115 DF

TABLE 5B

LSD Pair-wise Comparison of Thickness (Run 2)

| Name of Variety | Mean    | Homogeneous Groups |
| --------------- | ------- | ------------------ |
| PYC 6651        | 8.8500  | B                  |
| Challenger      | 9.98250 | A                  |

Alpha = 0.05
Standard Error for Comparison = 0.3783
Critical T Value = 1.992
Critical Value for Comparison = 0.7536
Error terms used: Error, 75 DF

TABLE 6A

LSD Pair-wise Comparison of Width (Run 1)

| Name of Variety | Mean   | Homogeneous Groups |
| --------------- | ------ | ------------------ |
| PYC 6651        | 18.233 | B                  |
| Challenger      | 22.900 | A                  |

Alpha = 0.05
Standard Error for Comparison = 0.3966
Critical T Value = 1.981
Critical Value for Comparison = 0.7856
Error terms used: Error, 115 DF

TABLE 6B

LSD Pair-wise Comparison of Width (Run 2)

| Name of Variety | Mean   | Homogeneous Groups |
| --------------- | ------ | ------------------ |
| PYC 6651        | 18.100 | B                  |
| Challenger      | 22.450 | A                  |

Alpha = 0.05
Standard Error for Comparison = 0.5142
Critical T Value = 1.992
Critical Value for Comparison = 1.0243
Error terms used: Error, 75 DF

TABLE 7A

LSD Pair-wise Comparison of Height (Run 1)

| Name of Variety | Mean   | Homogeneous Groups |
| --------------- | ------ | ------------------ |
| PYC 6651        | 102.07 | A                  |
| Challenger      | 81.40  | B                  |

Alpha = 0.05
Standard Error for Comparison = 0.7246
Critical T Value = 1.981
Critical Value for Comparison = 1.4352
Error terms used: Error, 115 DF

TABLE 7B

LSD Pair-wise Comparison of Height (Run 2)

| Name of Variety | Mean   | Homogeneous Groups |
| --------------- | ------ | ------------------ |
| PYC 6651        | 102.83 | A                  |
| Challenger      | 81.67  | B                  |

Alpha = 0.05
Standard Error for Comparison = 0.8274
Critical T Value = 1.992
Critical Value for Comparison = 1.6482
Error terms used: Error, 75 D

TABLE 8

LSD Pair-wise Comparison of *Fusarium* Resistance
(on a scale of 1 to 5, 5 being most resistant)

| Name of Variety | Mean | Homogeneous Groups |
|---|---|---|
| Napoleon | 4.6667 | A |
| Challenger | 1.3333 | B |
| PYC 6651 | 1.0167 | C |

Alpha = 0.05
Standard Error for Comparison = 0.0842
Critical T Value = 1.973
Critical Value for Comparison = 0.1662

Stix is similar to the celery cultivar "Challenger." However, Stix is significantly taller (102.5 cm vs. 46.2 cm), has more stalks longer than 40 cm (11.6 vs. 10.1), has longer petioles to the first joint (46.2 cm vs. 33.3 cm), and is more resistant to *Fusarium oxysporum* f. sp. *apii*, Race 2 (1.1 vs. 1.5 on a 1-5 scale, with 1 being highly resistant) as compared to Challenger.

Horticultural trait data was collected in 2007 and 2008. The first trial was planted on Feb. 14, 2007, and transplanted to a field belonging to Betteravia Farms in Santa maria, Calif. on Apr. 19, 2007. Data was collected on Jul. 9, 2007. The second trial was planted on Feb. 22, 2008, and transplanted to a field belonging to Betteravia Farms in Santa Maria, Calif. on May 13, 2008. Data was collected on Jul. 24, 2008.

The experimental design for both trials was a Randomized Complete Block. The trial in 2007 utilized four replications with 15 plants per replication. The trial in 2008 utilized four replications with 10 plants per replication. An Analysis of Variance (ANOVA) for a Randomized Complete Block (RCBD) design was performed on data from each of the trials. All pair-wise comparisons were performed to evaluate the Least Significant Differences (LSD) with an Alpha value of 0.05 (see Tables above). The commercially available software program Statistix 9 was used for the analyses.

*Fusarium* resistance was collected in 2007 and 2008. In addition to Stix and Challenger, the cultivar "Napoleon" was included as a susceptible control. Both trials were planted in a field known to have high levels of *Fusarium oxysporum* f. sp. *apii*, Race 2. The first trial was planted on Apr. 10, 2007 and transplanted on Jun. 15, 2007. Data was collected on Sep. 17, 2007. The second trial was planted on Apr. 8, 2008 and transplanted on Jun. 18, 2008. Data was collected on Sep. 24, 2008. Resistance was evaluated using the following method of scoring:

1=Plant appears healthy and shows no evidence of *Fusarium* in crown
2=plant appears healthy, but shows slight traces of discoloration in vascular tissue of crown due to *Fusarium*
3=plant appears healthy, but shows obvious discoloration in crown due to *Fusarium*
4=plant shows moderate stunting and yellowing and pronounced discoloration in crown
5=plant is severely stunted and yellowed with pronounced discoloration in crown along with secondary decay The experimental design for both *Fusarium* trials was a Randomized Complete Block. The trial in 2007 utilized four replications with 15 plants per replication. The trial in 2008 utilized three replications with 10 plants per replication. A One-Way Analysis of Variance was performed on data from each of the trials. All Pair-wise comparisons were performed to evaluate the Least Significant Differences (LSD) with an Alpha value of 0.05 (see Tables above). The software program Statistix 9 was used for the analyses.

Population Selection

Stix (PYC 6651) celery was developed via the Pedigree Breeding Method utilizing Single Plant Selections followed by Mass Selection procedures.

Figure 1:
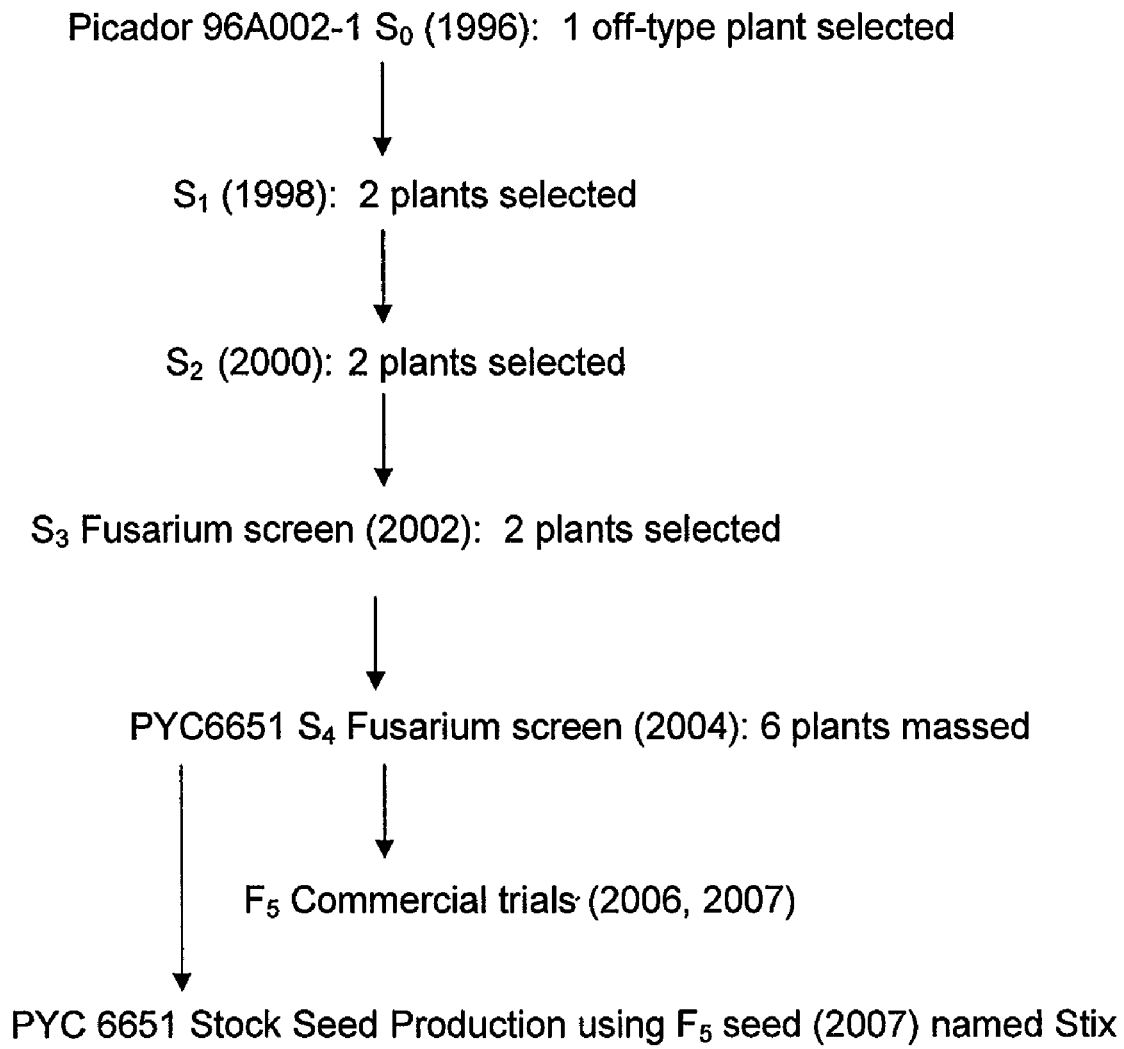
FIG. 1 shows a flowchart depicting the breeding history of Stix.

In the summer of 1996, a single extra-tall off-type plant (generation S0) was selected from a field of the celery variety "Picador" grown at Leach Farms in Berlin, Wis. This plant was identified as 96A002-1. Its petioles and roots were trimmed and it was taken to California where it was transplanted into a pot and grown over winter outdoors to induce bolting.

In February of 1997, the extra-tall S0 Picador was transplanted again from the pot into a celery nursery. It bolted that spring and was caged singly before flowering in a 3'×3'×6' 20-mesh insect proof cage to assure self pollination.

The (S1) seed from this cage was harvested and cleaned in the fall of 1997, and the S1 seed was planted into a trial in Berlin, Wis. in the spring of 1998. The S1 plot was quite variable in height and plants tended to produce a large number of suckers at the base. Two plants that appeared to be cleaner around their bases and had good height were selected at maturity in August of 1998.

The two selected plants were each singly caged in a 3'×3'×6' 20-mesh insect proof cage and flowered in the spring of 1999. S2 seed was harvested from them in the fall of 1999.

One of the two S2 seed lots was planted into a trial in Decatur, Mich. in the spring of 2000. It was fairly uniform with most plants having very long, slender petioles. Most of the plants again tended to produce sucker growth around the base. Two plants were selected on the basis of height and presence of fewer suckers. These plants were again each singly caged in a 3'×3'×6' 20-mesh insect proof cage, and S3 seeds were harvested from them in the fall of 2001.

After two generations (S1 and S2) of selection for horticulturally acceptable traits (i.e., selection against suckering and for tall petioles), two lines of S3 generation seed were planted to a *Fusarium* trial for screening in Santa Maria, Calif. in June 2002. The S3 seeds were planted in a field with *fusarium* presence to test for *fusarium* resistance.

One of these S3 plots demonstrated excellent field resistance to *Fusarium oxysporum* f. sp. *apii* in the trial. The plot was somewhat variable for petiole length and still showed sucker growth at the base. From this plot two plants were selected in September, again primarily for petiole length and presence of fewer suckers. The two plants were overwintered outdoor in pots, individually caged in 2003, and produced S4 seeds. The S4 seeds were harvested in October of 2003.

These S4 lots were planted again in the *fusarium* field in Santa Maria in 2004. There was good uniformity within and between the two lots. Both lots demonstrated excellent *fusarium* resistance and were unusually tall with long slender petioles. There was a noticeably reduced tendency for sucker growth. One of the lines was given the experimental designation PYC 6651. Six plants were selected from it and caged in mass in a large pollination cage in 2004. F5 seeds were harvested from that cage in the fall of 2005 (celery is a biennial plant).

The F5 lot has served as the source for trialing in 2006 and 2007 and as stock seed for a commercial size increase in 2007.

Criteria for selection during the development of Stix (PYC 6651) included 1) an exceptionally tall dark green celery with long, medium-smooth, slender petioles, and 2) a very high level of resistance to the *Fusarium* disease of celery.

Although the foregoing invention has been described in some detail by way of illustration and examples for purposes of clarity and understanding, it will be apparent that modifications and alternative embodiments of the invention are contemplated which do not depart from the spirit and scope of the invention as defined by the foregoing teachings and appended claims.

Applicants made a deposit of 2500 seeds of celery cultivar "STIX (PYC 6651)" with the American Type Culture Collection (ATCC), Manassas, Va., 20110-2209 U.S.A., ATCC Deposit No: PTA-9654 on Dec. 10, 2008.

What is claimed is:

1. A seed of celery cultivar "STIX (PYC 6651)", wherein a representative sample of seed has been deposited under ATCC accession number PTA-9654.
2. A celery plant produced by growing the seed of claim 1.
3. A plant part from the plant of claim 2.
4. A celery plant having all of physiological and morphological characteristics of the celery plant of claim 2.
5. A plant part from the plant of claim 4.
6. Pollen of the plant of claim 2.
7. An ovule of the plant of claim 2.
8. A tissue culture of regenerable cells of the plant of claim 2.

* * * * *